United States Patent [19]
Klemann et al.

[11] 4,060,674
[45] Nov. 29, 1977

[54] ALKALI METAL ANODE-CONTAINING CELLS HAVING ELECTROLYTES OF ORGANOMETALLIC-ALKALI METAL SALTS AND ORGANIC SOLVENTS

[75] Inventors: Lawrence P. Klemann, Somerville; Gerald H. Newman, Westfield, both of N.J.

[73] Assignee: Exxon Research and Engineering Company, Linden, N.J.

[21] Appl. No.: 750,517

[22] Filed: Dec. 14, 1976

[51] Int. Cl.$^2$ ................................................ H01M 6/14
[52] U.S. Cl. ...................................... 429/194; 429/198
[58] Field of Search .................................. 429/194–198

[56] References Cited
U.S. PATENT DOCUMENTS

| | | | |
|---|---|---|---|
| 3,764,385 | 10/1973 | Langer et al. | 429/194 X |
| 4,002,492 | 1/1977 | Rao | 429/194 |

*Primary Examiner*—C. F. LeFevour
*Attorney, Agent, or Firm*—Kenneth P. Glynn

[57] ABSTRACT

Electrolyte compositions for reversible alkali metal cells, e.g., lithium batteries, are described which consist essentially of (a) organic solvents selected from the group consisting of inertly substituted and unsubstituted ethers, esters, sulfones, organic sulfites, organic sulfates, organic nitrites and organic nitrates; and (b) electrolytically active alkali metal salts including organometallic alkali metal salts having the formula $ZMR_n$ wherein Z is an alkali metal, M is a metal selected from the group consisting of Zn, Cd, B, Al, Ga, In, Tl, Sn (stannous), P and As, the Rs are certain organic radicals, and $n$ is a numerical value equal to one plus the valence of the metal M. Rechargeable, high energy density electrochemical cells containing an anode having an alkali metal as its active material, a cathode, e.g., one having as its active material a transition metal chalcogenide, and an electrolyte composition of the above-described type, are also described.

15 Claims, No Drawings

ALKALI METAL ANODE-CONTAINING CELLS HAVING ELECTROLYTES OF ORGANOMETALLIC-ALKALI METAL SALTS AND ORGANIC SOLVENTS

BACKGROUND OF THE INVENTION

1. Field of the Invention

The present invention relates to novel electrolyte compositions for high energy density electrochemical cells and to cells including these electrolyte compositions. More specifically, the present invention is directed to electrolyte compositions consisting essentially of solvent and electrolytically active alkali metal salts including an organometallic alkali metal salt. It is also directed to rechargeable, high energy density electrochemical cells having alkali metal anodes and containing these electrolyte compositions.

2. Prior Art

A recently developed rechargeable, high energy density electrochemical cell consists of an alkali metal material as the anode-active material, a transition metal chalcogenide as the cathode-active material, and a nonaqueous electrolyte. More specifically, preferred cells consist of lithium anodes, titanium disulfide cathodes and nonaqueous electrolyte compositions consisting of various lithium salts, such as LiClO$_4$, dissolved in organic solvents, such as propylene carbonate, tetrahydrofuran, dioxolane, and mixtures of dimethyoxyethane and tetrahydrofuran, and containing various stabilizing additives.

Important features of these cells include their ability to be repeatedly discharged and charged. Theoretically, cycling by discharging and charging should be possible indefinitely, but in practice indefinite cycling is not realized. Dendritic growth on the anode during charging and degradation of the cathode material are sometimes limiting factors in the amount of cycling to which a cell can be subjected. However, the electrolyte, particularly nonaqueous electrolytes, can at times be the limiting factor. The effects of a particular electrolyte composition on the electrochemical performance of a cell may be significant due to its relative stability or it may be due to other factors. One particular electrolyte composition might be highly effective with a given anode-cathode couple but be ineffective for another couple, either because it is not inert to the second couple or because it reacts with itself under the conditions present during cycling. Furthermore, even when a particular electrolyte composition is effective in a given cell, it may nonetheless be undesirable for other reasons. For example, the sometimes preferred LiClO$_4$ based electrolyte creates a potential explosion hazard. And, for example, various organometallic alkali metal salt compounds such as are described in U.S. Pat. Nos. 3,734,963 and 3,764,385 have the disadvantage of requiring complexing with various nitrogen, phosphorus or sulfur-containing organic compounds containing at least two functionalities. Recent studies have been made directed to LiB(C$_6$H$_5$)$_4$ electrolyte systems by Szwarc et al, *J. Phys. Chem.*, Vol. 69, p 608 et seq. (1965) but these systems have been found to have low solubility and high resistivity. For these reasons, novel but effective lithium salt-containing electrolyte compositions for alkali metal anode type cells are desirable.

SUMMARY OF THE INVENTION

The present invention is directed to improved electrolyte compositions and to electrochemical cells containing these electrolyte compositions.

The electrolyte compositions consist essentially of organic solvent and electrolytically active alkali metal salts including an organometallic alkali metal salt of the formula:

$$ZMR_n \tag{1}$$

wherein Z is an alkali metal, M is a metal selected from the group consisting of Zn, Cd, B, Al, Ga, In, Tl, Sn (stannous) P and As, R represents organic radicals, as set forth below, and n is the number of organic radicals, i.e., n is a numerical value equal to one plus the valence of the metal M.

The alkali metal represented by Z in Formula (1) above is any alkali metal, but is desirably selected from lithium, sodium and potassium, with lithium being the preferred embodiment.

The metal M in Formula (1) is any of zinc, cadmium, boron, aluminum, gallium, indium, thallium, tin (stannous), phosphorus and arsenic. Desirably, M is selected from the group consisting of boron, aluminum, phosphorus and arsenic. Most preferred is boron.

The organic radicals represented by each R may be the same or different and are inertly substituted or unsubstituted organic radicals, with the proviso that at least one R is an alkyl radical. By "inertly substituted" is meant radicals containing substituents which have no detrimental effect on the electrolytic properties of the electrolyte composition in the context of its effectiveness in electrochemical cells. These organic radicals R may be, therefore, inertly substituted or unsubstituted alkyl radicals, aryl radicals, alkaryl radicals or aralkyl radicals, subject to the above proviso. For example, they may be selected from the group consisting of alkyl radicals having 1 to 8 carbon atoms, aryl radicals having 6 to 18 carbon atoms, and alkaryl and aralkyl radicals having 7 to 50 carbon atoms. Desirable organic radicals are the alkyl radicals having 1 to 6 carbon atoms, and the phenyl radical. Preferred are the organic radicals which are alkyl radicals having 1 to 4 carbon atoms. Particularly useful are the salts wherein all of the organic radicals are methyl radicals.

The variable n in Formula (1) represents the number of organic radicals R and is, therefore, a numerical value equal to one plus the valence of the metal M. Thus, n=3 when M is Zn, Cd, and Sn, n=4 when M is B, Al, Ga, In, and Tl, and n=6 when M is P and As.

The organometallic alkali metal salts employed in the present invention are prepared by reacting monoorganoalkali metal compounds with polyorgano-metallic compounds in an organic solvent. The reaction is believed to be represented by the following equation:

$$ZR + MR_{n-1} \rightleftarrows Z^+[MR_n]^- \tag{A}$$

wherein the variables are as defined for Formula (1) above. The reaction may be carried out at any operable pressure and temperature, and room temperature and pressure conditions will allow the reaction to readily occur in most instances.

As mentioned, the electrolyte composition of the present invention consists essentially or organic solvent and electrolytically active alkali metal salts including an organometallic alkali metal salt of Formula (1) above. Thus, a mixture of salts is contemplated, at least one of which is a Formula (1) type salt. The other salt or salts in the mixture may be any electrolytically active alkali metal salt which is compatible with the Formula (1) type salt, e.g., LiBr, LiI and the like. Also contemplated is the electrolyte which contains only one or more salts of Formula (1). Thus the expression "electrolytically active alkali metal salts including an organometallic alkali metal salt" should be construed to include: (1) mixtures of organometallic alkali metal salt(s) and other compatible alkali metal salt(s), and (2) one or more organometallic salts without other salts. Preferred is the electrolyte containing the organometallic salt(s) without other salts.

The organic solvent employed in the electrolyte composition of the present invention is generally one selected from the group consisting of inertly substituted and unsubstituted ethers, esters, sulfones, organic sulfites, organic sulfates, organic nitrites and organic nitrates. By "inertly substituted" solvent is meant one which contains substituents which have no detrimental effect on the electrolytic properties of the electrolyte composition in the context of its effectiveness in electrochemical cells. These solvents may be any of the foregoing which will function as either a diluent or as a complexing solvent with the organometallic alkali metal salt and which will, with the salt, produce an effective electrolyte. Thus, the solvents which are included are those composed of one or more compounds selected from straight chain ethers, polyethers, and cyclical ethers; including such ethers as the acetals, ketals and orthoesters; and organic esters, sulfones, organic nitrates and nitrites and organic sulfates and sulfites. Examples include propylene carbonate, tetrahydrofuran, dioxolane, furan, sulfolane, dimethyl sulfite, nitrobenzene, nitromethane and the like. The preferred solvents are the ethers. For example, dioxolane, dimethyoxyethane, and mixtures of these are useful. Preferred is a solvent containing dioxolane.

In general, sufficient organic solvent must be utilized to effectively render the organometallic alkali metal salt electrolytically active (i.e., adequately conductive) when employed in an electrolytic cell. The solvent may be a mixture of compounds as suggested above, and may contain known electrolyte additives which are compatible with the solvent and the particular salt employed. As to the amount of salt to be employed in the organic solvent, this will vary tremendously with the specific solvent used, the salt chosen and the type of electrochemical cell performance which is desired. In any event, an electrolytically active amount of salt must be added to the solvent. Typically, at least about 0.1 moles of salt up to saturation may be used per liter of solvent, e.g., about 0.1 to about 5 moles/liter may be used and preferably about 0.5 to about 3 moles/liter may be used.

The present invention, as mentioned, also relates to improved, rechargeable, high energy density electrochemical cells. The cells include any containing alkali metal anodes and electrolytes as defined above. Particularly useful are those containing solid cathode-active materials, e.g., cathodes having transition metal chalcogenides. Also preferred are the secondary cells. Alkali metals used in the anodes are desirably lithium, sodium and potassium, and the transition metal chalcogenide cathode-active materials include those containing at least one member selected from the group consisting of molybdenum, titanium, zirconium, hafnium, niobium, tantalum and vanadium; and at least one chalcogen selected from oxygen, sulfur, selenium, and tellurium. The anode is advantageously made of lithium or lithium alloys because lithium has the lowest equivalent weight of the alkali metals and is the most electronegative, thereby providing the most energy per weight unit. Of the lamellar transition metal chalcogenides, preferred are the dichalcogenides, and the most preferred is titanium disulfide because it has a low equivalent weight, is electrically conductive and its constituents are readily available. The electrolyte composition consists essentially of solvent and alkali metal salt(s) which is set forth above.

The following examples are presented as merely being illustrative of the present invention, and the invention should not be construed to be limited thereto. Examples 1 and 2 are directed to prior art electrolytes and Examples 3 to 9 exemplify the present invention (Example 8 illustrates an electrolyte of the present invention which contains a mixture of salts.) Examples 10 to 21 are directed to comparisons of prior art type electrolyte systems and those of the present invention.

EXAMPLE 1

$LiB(C_6H_5)_4$ (lithium tetraphenylboride) was prepared in accordance with the teachings of Szwarc et al, cited above, by reacting $NaB(C_6H_5)_4$ with LiCl. A dry, solvent free salt was obtained at a yield of 91.4%. The salt was dissolved in dioxolane and was found to have a limited solubility. A saturated dioxolane solution contained about 1.14 moles of salt per liter of solvent. Because a low resistivity is important in any successful electrolyte system, specific resistivities were measured as a function salt concentration in the solvent and the results are represented in Table I below.

EXAMPLE 2

$TMED.LiB(C_2H_5)_3C_6H_5$ (tetramethylethylenediamine lithium triethylphenylboride) represents the prior art electrolyte of the type described in U.S. Pat. No. 3,764,385. To a solution of triethylboron (19.66 g, 0.2 mol) in 250 ml of benzene was added dropwise 100 ml of a 2 M benzene solution of $TMED.LiC_6H_5$. After stirring overnight, the solution was warmed to 50° C for 45 minutes. Solvent removal on a vacuum rotary evaporator gave $TMED.LiB(C_2H_5)_3C_6H_5$ as a white solid.

Analysis: Calculated for $C_{18}H_{36}N_2BLi$: C, 72.49; H, 12.17; and N, 9.39%. Found: C, 72.15; H, 11.99; and N, 8.94%.

Specific resistivities were obtained in dioxolane as a function of $TMED.LiB(C_2H_6)_3C_6H_5$ concentration expressed as moles complex per liter solvent. The results are given in Table I below.

EXAMPLE 3

Lithium tetramethylboride representing an electrolyte salt of the present invention was prepared as follows:

Boron trifluoride diethyletherate (70.9 g, 0.5 mole) was added slowly to a stirred solution of $CH_3MgBr$ (525 ml of 2.68 M ether solution) under a dry argon atmosphere. The volatile $B(CH_3)_3$ which formed was passed by means of a glass transfer line to a second flask where it was allowed to react with an ether solution of halide free $CH_3Li$ (315 ml of 1.59 M solution) which was cooled by a bath of Dry Ice-acetone. The reaction mixture was allowed to stand overnight and warm slowly to room temperature. The bulk of the ether was removed by distillation. Final vacuum drying (~0.1 Torr, 60° C) afforded 33.4 g (85%) of LiB(CH$_3$)$_4$ as white crystals.

Pure LiB(CH$_3$)$_4$ melts at 182°-4° C and forms clear solutions in dioxolane. Specific resistivity measurements made on such solutions are given in Table I below.

dioxolane and specific resistivities of the solution were measured. The data is given in Table I. A solution containing greater than 1.5 moles of salt per milliliter of dioxolane could not be obtained owing to limited solubility of the salt.

TABLE I
SPECIFIC RESISTIVITIES OF LITHIUM SALTS IN DIOXOLANE

| Example | Salt | Specific Resistivity ($\Omega$ cm) at | | | | | |
|---|---|---|---|---|---|---|---|
| | | 0.5 m' | 1.0 m' | 1.5 m' | 2.0 m' | 2.5 m' | 3.0 m' |
| 1 | LiB(C$_6$H$_5$)$_4$ Prior Art | 320 | 266 | — | — | — | — |
| 2 | TMED . LiB(C$_2$H$_5$)C$_6$H$_5$ Prior Art | — | 224 | — | 238 | — | 331 |
| 3 | LiB(CH$_3$)$_4$ | — | 120 | 106* | 94 | 103 | 121 |
| 4 | LiB(CH$_3$)$_3$C$_4$H$_9$ | — | 121 | 107 | 110 | 126 | 149 |
| 5 | LiB(C$_2$H$_5$)$_3$C$_4$H$_9$ | 168 | 113 | 114 | 136 | 184 | 268 |
| 6 | LiB(C$_4$H$_9$)$_4$ | — | 190 | 208 | 166 | 378 | 592 |
| 7 | LiB(C$_6$H$_5$)$_3$C$_4$H$_9$ | 347 | 295 | 356 | — | — | — |

*Concentration was 1.2 moles/liter slvent.

EXAMPLE 4

Boron trifluoride diethyletherate (28.4 g, 0.2 mol) was added slowly to a stirred ether solution containing about 0.6 mol of CH$_3$MgBr. The B(CH$_3$)$_3$ which formed was swept from the reaction flask in a stream of dry nitrogen and was condensed in ether contained in a second flask which was cooled by Dry-Ice. One-half hour after all the BF$_{3.(C_2H_5)_2O}$ had been added, butyllithium (125 ml, 1.6 M solution in hexane) was added to the B(CH$_3$)$_3$-ether solution. Solvent was removed in vacuo to leave 31.5 g of liquid product having the formula LiB(CH$_3$)$_3$C$_4$H$_9$.

This material was dissolved in dioxolane then the solution was evaporated, first on a vacuum rotary evaporator, then by means of a vacuum pump until a constant weight of 36.1 g was obtained. The product, a thick, opaque, liquid was formulated as LiB(CH$_3$)$_3$C$_4$H$_9$ dioxolane. Specific resistivity measurements obtained on dioxolane solutions of this material are given in Table I.

EXAMPLE 5

LiB(C$_2$H$_5$)$_3$C$_4$H$_9$. A solution of butyllithium (82 ml, 2.45 M in hexane) was added dropwise under nitrogen to a solution of triethylboron (19.6 g, 0.2 mol) in 500 ml of heptane. After the addition was complete, the slurry formed was diluted with 200 ml of heptane and the mixture was heated at 45° C for 2 hours. Filtration and vacuum drying the solid afforded 32.4 g (quantitative) of LiB(C$_2$H$_5$)$_3$C$_4$H$_9$. Specific resistivities of this salt in dioxolane were measured as a function of concentration and the results are given in Table I.

EXAMPLE 6

LiB(C$_4$H$_9$)$_4$. Butyllithium (125 ml, 1.6 M solution in hexane) was added to a solution of tributylboron (36.4 g, 0.2 mol) in 500 ml of heptane under a nitrogen atmosphere producing an immediate precipitate. The solid was isolated by filtration and was dried in a vacuum. The yield was 36.7 g (75%) of air sensitive solid. Specific resistivities of dioxolane solutions were measured and are given in Table I.

EXAMPLE 7

LiB(C$_6$H$_5$)$_3$C$_4$H$_9$. To a suspension of triphenylboron (4.8 g, 19.8mmol) in 75 ml of heptane was added 20 mmol of butyllithium in hexane (12 ml). After stirring overnight the product was filtered and dried in a vacuum. The solid, which weighed 2.09 g, was dissolved in

EXAMPLE 8

LiB(CH$_3$)$_4$·½ LiBr. Brown trifluoride diethyletherate (0.5 mole) was added slowly to a diethylether solution containing 2 moles of CH$_3$Li·LiBr under an atmosphere of dry nitrogen. A Dry Ice-acetone bath provided cooling during this addition and after addition was complete, the reaction mixture was allowed to warm to room temperature. The solution was decanted from excess lithium salts and was concentrated to about 400 ml by distillation. Filtration removed additional salt and afforded a clear solution which was concentrated to give a white solid. This solid, after drying at 60° C in a vacuum, weighed 42.7g.

Analysis, calculated for LiB(CH$_3$)$_4$·½ LiBr: Br, 32.93%. Found: Br, 32.18%.

Sufficient LiB(CH$_3$)$_4$·½ LiBr was dissolved in dioxolane to produce a solution which was 2.5 molar in lithium ion concentration. This solution had a specific resistivity of 109 ohm cm.

EXAMPLE 9

LiAl(CH$_3$)$_3$C$_4$H$_9$. Addition of butyllithium (62.5 ml of a 2.4 M hexane solution) to a stirred solution of trimethylaluminum (10.8g, 0.15 mole) in 850 ml of heptane gave an immediate precipitate. After an additional 2 hours stirring, the solid was isolated by filtration, was washed three times with fresh heptane and was vacuum dried to give about 17g of solid.

Specific resistivities of this salt were obtained as a function of concentration in dioxolane solution. They were found to be 129, 104, 110 and 139 ohm cm. resistivity at concentrations of 1.0 m', 1.5 m', 2.0 m' and 2.5 m' respectively.

EXAMPLES 10 Through 20

These examples are directed to the testing of various TMED-complexed prior art electrolyte-containing cells and present invention electrolyte-containing cells.

The test cells contained a lithium anode of lithium ribbon pressed on expanded nickel or tantalum screen. The cathode was a porous cake of a mixutre of TiS$_2$ and Teflon (90-95% TiS$_2$ and 5-10% Teflon) pressed onto an expanded nickel or tantalum screen or pressed onto a piece of carbon felt. The anode and cathode were separated by placing the anode and cathode in microporous polypropylene bags sold under the name Celgard by Celanese Corporation of America, New York. A glass mat was also placed between the anode and the cathode. The cells were also provided with a reference lithium electrode of lithium ribbon pressed on a tantalum or nickel screen. The reference was also in a microporous polypropylene bag and separated from the cathode by a glass mat. The reference electrode was located on the side of the cathode opposite the anode.

The results of the tests are set forth in Table II below. As can be seen, most of the electrolytes of the present invention are at least as good as, and in many cases better than, the TMED-complexed electrolytes. Thus, it was surprisingly discovered that the prior art complexing requirements were, in fact, not necessary to obtain advantageous electrolyte systems.

1.82 m' (146 ohm cm), 1.54 m' (133 ohm cm), 1.23 m' (125 ohm cm) and 0.87 m' (136 ohm cm).

The composition $LiB(C_2H_5)_3C_4H_9$ was dissolved in dioxolane to give a 3.0 m' solution. The specific resistivities of this solution and solutions prepared by subsequent dilution with dioxolane were measured: 3.0 m' (268 ohm cm), 2.5 m' (184 ohm cm), 2.0 m' (136 ohm cm), 1.5 m' (114 ohm cm), 1.0 m' (113 ohm cm) and 0.5 m' (168 ohm cm).

Plots of Specific Resistivity vs. volume molality were made for $TMED.LiB(C_2H_5)_3C_4H_9$ in benzene, $TMED.LiB(C_2H_5)_3C_4H_9$ in dioxolane and $LiB(C_2H_5)_3C_4H_9$ in dioxolane. Smooth curves could be drawn through

TABLE II

TEST CELL RESULTS FOR LITHIUM SALT-CONTAINING ELECTROLYTES[1]

| Example | Salt | % Primary | Theor. mA-Hrs | Accumulated A-Hrs/g | F.O.M. | Discharge Rate mA | # Cycles | Cathode Grid |
|---|---|---|---|---|---|---|---|---|
| 10 | 1.5m'TMED . LiB(CH$_3$)$_4$ | 56 | 275 | 1.14 | 4.8 | 32.5 | 19 | Ta |
|  |  | 59 | 184 | 1.27 | 5.3 | " | 33 | Ta |
| 11 | 1.5m'TMED . LiB(CH$_3$)$_4$ | 66 | 123 | 4.1 | 17.2 | " | 47 | C |
|  |  | 66 | 120 | 4.8 | 20.2 | " | 42 | C |
| 12 | 2m'TMED . LiB(C$_2$H$_5$)$_3$C$_4$H$_9$ | 63 | 234 | 1.41 | 5.9 | " | 21 | Ta |
|  |  | 61 | 226 | 1.24 | 5.2 | " | 42 | Ta |
| 13 | 2m'TMED . LiB(C$_4$H$_9$)$_4$ | 44 | 142 |  |  | " | 32 | Ni |
|  |  | 40 | 148 | 1.92 | 8.0 | " | 43 | Ni |
| 14 | 1.5'LiB(CH$_3$)$_4$ | 83 | 105 | 9.2 | 38.2 | " | 85 | C |
|  |  | 79 | 110 | 4.9 | 20.4 | " | 42 | C |
| 15 | 2.5m'LiB(CH$_3$)$_4$ | 97 | 238 | 1.5 | 6.3 | " | 11 | Ta |
|  |  | 88 | 232 | 2.5 | 5.4 | " | 23 | C |
|  |  | 90 | 222 | 2.0 | 8.2 | " | 25 | C |
| 16 | 2m'LiB(C$_2$H$_5$)$_3$C$_6$H$_5$ | 63 | 219 |  |  | " | 10 | Ni |
|  |  | 64 | 210 |  |  | " | 5 | Ni |
| 17 | 2m'LiB(C$_2$H$_5$)$_3$C$_4$H$_9$ | 48 | 107 |  |  | " | 5 | Ni |
| 18 | 2m'LiB(C$_2$H$_5$)$_3$C$_4$H$_9$ . 2LiBr | 48 | 110 |  |  | " | 3 | Ni |
| 19 | 2m'LiB(C$_2$H$_5$)$_3$C$_4$H$_9$ . LiI | 36 | 102 |  |  | " | 4 | Ni |
| 20 | 1.67m'LiB(CH$_3$)$_4$ . 0.83M LiBr | 93 | 230 | 1.0 | 4.0 | 32.5 | 13 | Ta |
|  |  | 65 | 118 | 2.74 | 11.4 | 65 | 38 | Ta |
|  |  | 83 | 142 | 4.0 | 16.8 | 32.5 | 50 | Ta |

[1]Definition for column headings:
% Primary — the material utilization of the cell in the first discharge as calculated by the number of m-amps-hrs of discharge divided by the theoretical amount possible determined by the weight of TiS$_2$ present.
Theor. (mA-Hrs) — ma-Hrs possible in cell from wt. of TiS$_2$.
Accumulated A-Hrs./g. — (Accumulated Amp-Hr./g.) - is equal to the material utilization (M.U.) achieved at the termination of testing multiplied by the average M.U. multiplied by the theoretical amp-hrs./g. of TiS$_2$. Accumulated A-hr/g = # cycles to X M.U. × average M.U. × theoretical A-hr./g. TiS$_2$.
F.O.M. (Figure of Merit) — the accumulated A-hrs./g. divided by the theoretical A-hr./g. of TiS$_2$.
Discharge Rate — total current during discharge of cells. All cathodes were 1 in.$^2$ in area.
Cycles — the total number of charge-discharge cycles that the cell was subjected to and were included in the calculations of the figure of merit (FOM).
Cathode Grid — the material used as the electronic collector material of the cathode.

EXAMPLE 21

An electrolyte composition of the present invention containing $LiB(C_2H_5)_3C_4H_9$, a composition containing this salt complexed with TMED as in the prior art and dissolved in the prior art benzene solvent, and a composition containing this salt complexed with TMED but dissolved in a preferred solvent of the present invention were prepared and tested for comparison as follows:

A two molar solution of $TMED.LiB(C_2H_5)_3C_4H_9$ in benzene was prepared. A portion of this solution was used to make serial dilutions to 1.5 molar and 1.0 molar solute concentrations. Specific resistivities for the 2.0, 1.5 and 1.0 M solutions were 1450, 1075 and 1175 ohm centimeters, respectively. In a subsequent experiment, 0.576 g (2 mmole) of the same complex was dissolved in 0.308g (0.35 ml) of benzene to give a 2.0 molar solution. By combining the 0.35 ml benzene with the 0.30 ml of TMED contained in $TMED.LiB(C_2H_5)_3C_4H_9$, the total solvent present becomes 0.65 ml. and the solution molality of 3.08 m'. Expressing the 1.5 and 1.0 molar solutions in terms of volume molalities one obtains 2.94 and 1.48 m', respectively.

Solutions of $TMED.LiB(C_2H_5)_3C_4H_9$ in dioxolane were prepared and the volume molalities were corrected for the TMED diluent. For each solution, the specific resistivity was measured: 2.07 m' (175 ohm cm), these data. The data allowed comparison of Specific Resistivities within the concentration range of 1.25–2.0 m'. The data, interpolated from these plots, are summarized in Table III below.

TABLE III

RESISTIVITIES OF $LiB(C_2H_5)_3C_4H_9$ AS FUNCTION OF COMPLEXING AGENT AND SOLVENT

| Volume Molalities m' | Specific Resistivities (ohm cm) | | |
|---|---|---|---|
|  | TMED . Li Salt Benzene | TMED . Li Salt Dioxolane | Li Salt Dioxolane |
| 1.25 | 1160 | 125 | 110 |
| 1.50 | 1105 | 130 | 114 |
| 1.75 | 1080 | 140 | 120 |
| 2.0 | 1075 | 170 | 136 |

The table illustrates that $TMED.LiB(C_2H_5)_3C_4H_9$ in benzene clearly is more resistive than the same complex dissolved in dioxolane. Furthermore, comparing $TMED.LiB(C_2H_5)_3C_4H_9$ in dioxolane vs. $LiB(C_2H_5)_3C_4H_9$ in dioxolane, the presence of TMED offers no advantage and actually increases the resistivity of the lithium salt.

What is claimed is:

1. In an electrochemical cell which contains an alkali metal anode, a cathode and a non-aqueous electrolyte, the improvement comprising;

using as said electrolyte one which consists essentially of:
a. an organic solvent selected from the group consisting of inertly substituted and unsubstituted ethers, sulfones, organic sulfates, organic sulfites, organic nitrates and organic nitrites; and
b. electrolytically active alkali metal salts including an electrolytically active amount of an organometallic alkali metal salt having the formula:

$$ZMR_n$$

wherein Z is an alkali metal, wherein M is a metal selected from the group consisting of Zn, Cd, B, Al, Ga, Sn (stannous), In, Tl, P and As, wherein R represents $n$ number of radicals which may be the same or different and are inertly substituted or unsubstituted organic radicals selected from the group consisting of alkyl radicals having 1 to 8 carbon atoms, aryl radicals having 6 to 18 carbon atoms, and alkaryl and aralkyl radicals having 7 to 50 carbon atoms, subject to the proviso that at least one R is an alkyl radical, and wherein $n$ is a numerical value equal to one plus the valence of the Metal M.

2. The cell of claim 1 wherein the cathode comprises a solid cathode-active material.

3. The cell of claim 2 wherein in the electrolyte, Z is an alkali metal selected from the group consisting of lithium, sodium, and potassium, M is a metal selected from the group consisting of B, Al, P and As, and wherein the organic radicals R may be the same or different and are inertly substituted or unsubstituted organic radicals selected from the group consisting of alkyl radicals having 1 to 6 carbon atoms and a phenyl radical.

4. The cell of claim 3 wherein the cell is a secondary cell and the organic solvent is an ether.

5. The cell of claim 4 wherein, in the electrolyte, Z is lithium, wherein M is boron, and wherein the organic radicals R may be the same or different and are inertly substituted or unsubstituted organic radicals selected from the group consisting of alkyl radicals having 1 to 4 carbon atoms.

6. The cell of claim 5 wherein said organic solvent is one or more ethers and wherein all of the organic radicals R are methyl radicals.

7. In an electrochemical cell which includes an anode having at least one alkali metal as its active material, a cathode having a lamellar transition metal chalcogenide as the cathode-active material and an electrolyte composition, the improvement wherein said electrolyte composition consists essentially of:
a. an organic solvent selected from the group consisting of inertly substituted and unsubstituted ethers, sulfones, organic sulfates, organic sulfites, organic nitrates and organic nitrites; and
b. electrolytically active alkali metal salts including an electrolytically active amount of an organometallic alkali metal salt having the formula:

$$ZMR_n$$

wherein Z is an alkali metal, wherein M is a metal selected from the group consisting of Zn, Cd, B, Al, Ga, Sn (stannous), In, Tl, P and As, wherein R represents $n$ number of radicals which may be the same or different and are inertly substituted or unsubstituted organic radicals selected from the group consisting of alkyl radicals having 1 to 8 carbon atoms, aryl radicals having 6 to 18 carbon atoms, and alkaryl and aralkyl radicals having 7 to 50 carbon atoms, subject to the proviso that at least one R is an alkyl radical, and wherein $n$ is a numerical value equal to one plus the valence of the metal M.

8. The electrochemical cell of claim 7, in the electrolyte, wherein Z is an alkali metal selected from the group consisting of lithium, sodium, and potassium, M is a metal selected from the group consisting of B, Al, P and As, and wherein the organic radicals R may be the same or different and are inertly substituted and unsubstituted organic radicals selected from the group consisting of alkyl radicals having 1 to 6 carbon atoms and a phenyl radical.

9. The electrochemical cell of claim 8 wherein the anode-active material is lithium or alloys thereof, wherein the cathode-active material is titanium disulfide, and wherein, in the electrolyte, Z is lithium.

10. The electrochemical cell of claim 8 wherein, in the electrolyte, Z is lithium, wherein M is boron and wherein the organic radicals R may be the same or different and are inertly substituted or unsubstituted organic radicals selected from the group consisting of alkyl radicals having 1 to 4 carbon atoms.

11. The electrochemical cell of claim 8 wherein the concentration of the organometallic alkali metal salt in said solvent is about 0.1 to about 5 moles/liter.

12. The electrochemical cell of claim 9 wherein said organic solvent is one or more ethers.

13. The electrochemical cell of claim 10 wherein said organic solvent is one or more ethers and wherein all of the organic radicals R are all methyl radicals.

14. The electrochemical cell of claim 13 wherein the solvent contains dioxolane.

15. The electrochemical cell of claim 11 wherein the concentration of the organometallic alkali metal salt in said solvent is about 0.5 to about 3 moles/liter.

* * * * *